US009558922B2

(12) United States Patent
Anderson et al.

(10) Patent No.: US 9,558,922 B2
(45) Date of Patent: Jan. 31, 2017

(54) QUANTITATIVE PEPTIDE ANALYSIS BY MASS SPECTROMETRY BASED ON BELL-FUNCTION FITTING FOR ION ISOTOPE DISTRIBUTION

(75) Inventors: Leigh Anderson, Washington, DC (US); Detlev Suckau, Grasberg (DE)

(73) Assignees: Bruker Daltonik GmbH, Bremen (DE); Anderson Forschung Group LLC, Washington, DC (US)

( * ) Notice: Subject to any disclaimer, the term of this patent is extended or adjusted under 35 U.S.C. 154(b) by 1159 days.

(21) Appl. No.: 13/484,357

(22) Filed: May 31, 2012

(65) Prior Publication Data

US 2012/0309027 A1    Dec. 6, 2012

Related U.S. Application Data

(60) Provisional application No. 61/492,582, filed on Jun. 2, 2011.

(51) Int. Cl.
| | | |
|---|---|---|
| *G01N 24/00* | (2006.01) | |
| *H01J 49/00* | (2006.01) | |
| *G01N 33/68* | (2006.01) | |

(52) U.S. Cl.
CPC ....... *H01J 49/0036* (2013.01); *G01N 33/6851* (2013.01); *H01J 49/0009* (2013.01)

(58) Field of Classification Search
CPC .................. Y10T 436/24; Y10T 436/143333; Y10T 436/105831; Y10T 436/10; Y10T 436/104165; Y10T 436/104998; Y10T 436/11; Y10T 436/113332; Y10T 436/203332; Y10T 436/25; Y10T 436/25125; Y10T 436/25875
See application file for complete search history.

(56) References Cited

U.S. PATENT DOCUMENTS

| | | | |
|---|---|---|---|
| 6,188,064 B1 * | 2/2001 | Koster | ........................... 250/282 |
| 6,287,872 B1 | 9/2001 | Schurenberg | |
| 6,825,465 B2 | 11/2004 | Schurenberg | |
| 7,235,781 B2 | 6/2007 | Haase | |
| 2008/0296488 A1 | 12/2008 | Holle | |

OTHER PUBLICATIONS

Gstaiger and Aebersold, "Applying mass spectrometry-based proteomics to genetics, genomics and network biology", Nature Reviews, Genetics, Sep. 2009, v. 10, pp. 617-627.*

* cited by examiner

*Primary Examiner* — Yelena G Gakh
(74) *Attorney, Agent, or Firm* — Benoit & Cote, Inc.

(57) ABSTRACT

A method for determining the concentration ratio in a sample of a target peptide to a reference peptide that is chemically identical with the target peptide, but labeled by isotopes, acquires mass spectra of the target and reference peptides. One of a plurality of families of superimposed bell-shaped curves which is a best fit to ion current peak groups of the target and reference peptides in the mass spectra is determined by varying parameters of the families. In each family, each bell-shaped curve has a predetermined height, the curves have fixed distances from each other and the relative curve heights and curve distances in the families are individually calculated from an elemental composition of the peptides and an isotope abundance distribution of elements composing the peptides, taking into account purity of the isotopes. The concentration ratio is then determined from the parameters of the best fit.

23 Claims, 3 Drawing Sheets

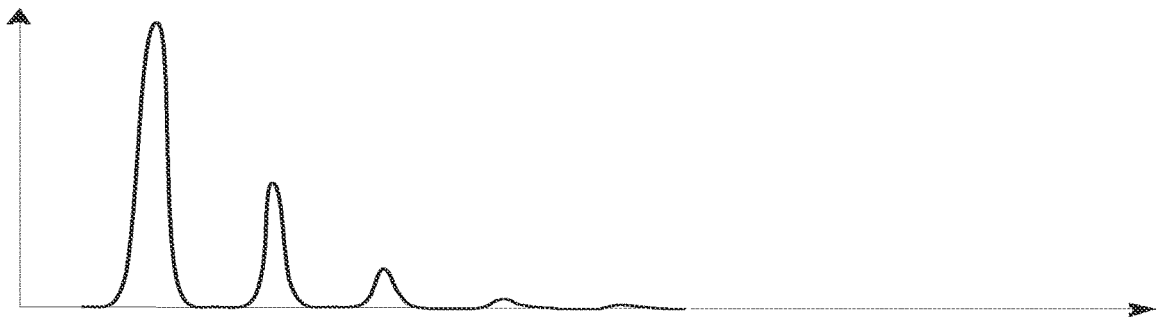
FIG. 1 *(Prior Art)*
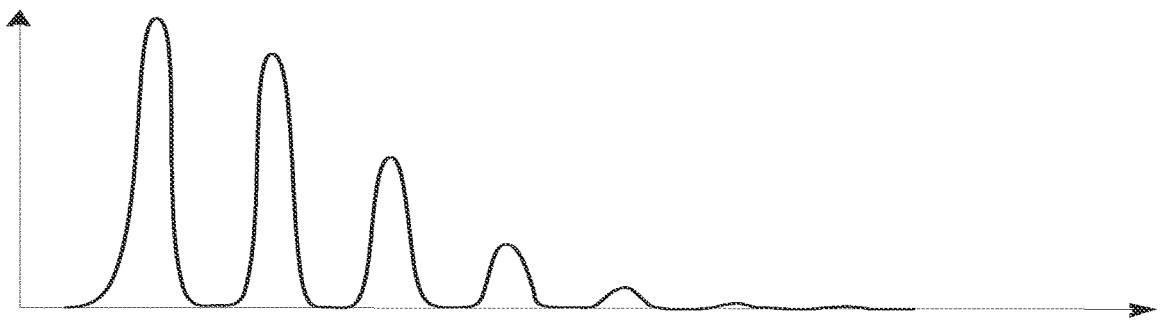
FIG. 2 *(Prior Art)*
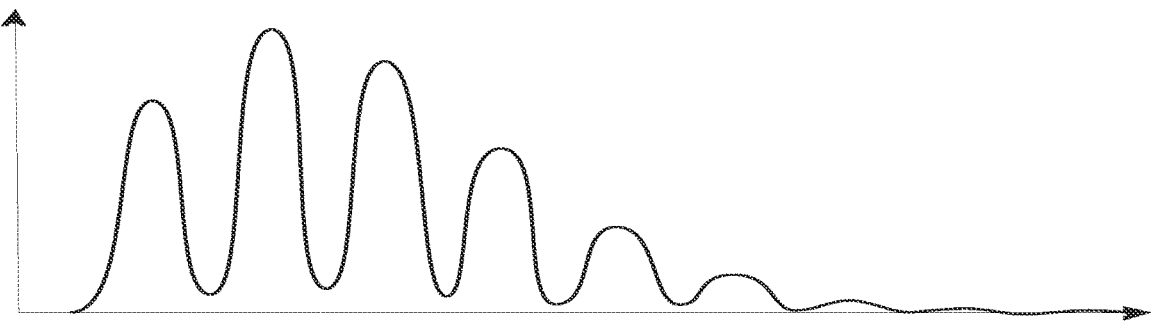
FIG. 3 *(Prior Art)*

QUANTITATIVE PEPTIDE ANALYSIS BY MASS SPECTROMETRY BASED ON BELL-FUNCTION FITTING FOR ION ISOTOPE DISTRIBUTION

BACKGROUND

The invention relates to an accurate determination of peptide concentrations in body fluids by mass spectrometry using internal reference substances. In medical research and medical diagnostics, protein concentrations in body fluids are usually determined by immuno assays, particularly by "Enzyme Linked Immuno-Sorbent Assays" (ELISA). Most often, because it is the safest method, a method called "Double Antibody Sandwich ELISA" is used, requiring two specific antibodies binding at two different epitopes of the protein molecule without sterical hindrance. The method is expensive, requires highly specific antibodies, does not allow for the application of internal references, and is not applicable for smaller peptides, because these rather tiny molecules in general do not offer two sufficiently separated specific binding epitopes for antibodies. Also, other types of immuno assays usually are not adaptable to these peptides.

Peptides—like the larger proteins—are biomolecules most essential for life. Blood and other body fluids contain many hundreds of physiologically active peptides: numerous peptide hormones, releasing hormones, neurotransmitters, and many others. Their concentration is highly informative about health or defects such as infections or other diseases; quite often small changes of the concentrations are decisive. A simple, safe, inexpensive, fast and highly precise analysis method, easily extensible to a multitude of different body fluid peptides, is urgently required. Occasionally, also peptide antibiotics and peptide toxins have to be analyzed quantitatively.

Diagnostic analysis procedures must fulfill strong quality standards. In most countries, permissions by state offices or official organizations are required to apply these methods in medical labs. In the USA, the FDA is responsible for the approval of medical analysis procedures. In some countries, state offices or official organizations must check the quality of a certain analytical procedure and the quality of the required devices according to rules which are specified by law.

In the field of bioorganic substances, mass spectrometry is most often directed to precise mass determinations for the identification of substances and only occasionally to quantitative analyses. Ionization methods for proteins and peptides, like electrospray ionization (ESI) or ionization by matrix assisted laser desorption (MALDI) were often regarded as non-quantitative. In fact, competitive processes during the ionization of mixtures of substances turn out to be advantageous for some substances and disadvantageous for others; so the degree of ionization depends on the mixture and the concentrations of the analyte substances. In the past, particularly MALDI was regarded as highly non-quantitative because early preparation methods of samples on mass spectrometric target plates ("dried droplets") did not produce homogeneous samples, and the yield of ions varied over orders of magnitude from sample spot to sample spot.

More modern sample preparations use hydrophilic sample areas on hydrophobic MALDI target plates (U.S. Pat. No. 6,287,872 B1; GB 2 332 273 B; DE 197 54 978 C1; M. Schürenberg and J. Franzen, 1998), allowing for very homogeneous thin layer preparations. MALDI target plates made from electrically conductive plastics are commercially available, pre-prepared with thin layers of HCCA on 384 spots with 0.8 millimeter diameter (U.S. Pat. No. 6,825,465 B2; GB 2 391 066 B; DE 102 30 328 B4; M. Schürenberg, 2002). HCCA is an acronym for α-cyano-4-hydroxycinnamic acid, a widely used matrix substance for the ionization of proteins and peptides by matrix assisted laser desorption (MALDI). These thin layer preparations, in connection with suitable lasers, show excellent precision of quantitative analyses procedures with coefficients of variations (CV) in the order of five to ten percent, if suitable reference substances are used.

The best quantitative analysis procedures for measuring concentrations of analyte substances in fluids are based upon reference substances, measured in the same spectrum (internal standard). Most favorable reference substances are isotopically labeled substances of otherwise exactly the same type as the targeted analyte substance. As an example, a reference peptide for a target peptide may be a synthetically produced target peptide with just one arginine comprising six $^{13}C$ and four $^{15}N$ atoms instead of the native six $^{12}C$ and four $^{14}N$ atoms. This reference peptide is 10 dalton heavier than the target peptide. In a mass spectrum, the isotope groups of both substances are clearly separated. The reference substance is added in exactly known amounts to the fluid with the analyte substance, e.g., a blood plasma. Both analyte and reference substance are now extracted from the fluid, e.g., using magnetic beads with immobilized antibodies for the analyte substance. The extraction does not need to be extremely specific because any cross-reaction with other substances will be immediately visible in the mass spectrum, and usually does not disturb the analytical procedure. The extracted substances will then be removed from the extraction sites, e.g., immobilized antibody layers, and a sample preparation of the extracted substances will be prepared on a thin layer spot on a MALDI target plate. The ratio of peak heights or peak areas in the mass spectrum can be determined, and from this ratio, the concentration of the analyte substance can be calculated. Because the extraction process has exactly the same yield for both the analyte and the chemically identical reference, and the mass spectrometric sensitivity is also identical with respect to ionization and detection, the ratio reflects (in first order) the ratio of the concentrations.

Any quantitative mass spectrometric analysis procedure requires a safe recognition of the analyte by an accurate mass determination. We now change the subject from precise determination of peptide concentrations to accurate mass determination. In fact, mass spectrometers can only determine the ratio m/z of the ion mass m to the number z of unbalanced elementary charges of the ion. Where the terms "mass of an ion" or "ion mass" are used here for simplification, they always refer to this ratio m/z of the mass m to the dimensionless number of elementary charges z of the ion. This charge-related mass m/z has the physical dimension of a mass; it is often also called "mass-to-charge ratio", although this is incorrect with regard to physical dimensions. In general, for the ionization of peptides by MALDI, z=1 is valid, in contrast to an ionization by electrospray (ESI), where most of the ions are multiply charged.

Any mass spectrometer delivers a series of ion current values forming a "spectrum". The scale parameter x of the spectrum depends on the kind of mass spectrometer, it may be spatial position p, as in mass spectrometers with ion detection by photoplates or diode arrays, a scan voltage V, as in RF ion traps, or a flight time t in case of time-of-flight mass spectrometers. In general, the term "spectrum" acquired by a mass spectrometer should denote any of these ion current spectra noted above, but also any transformation of the ion current spectrum into other forms, as, for example, a spectrum of the frequencies f in Fourier-transform mass spectrometers, including even the final spectrum of the masses m.

For an accurate mass determination of ions by a given mass spectrometer, the mass spectrometer first has to be calibrated with a mixture of known calibration substances, covering the mass range of interest. This calibration procedure results in a function between the charge-related mass m/z of the ions and the scale parameter x along the spectrum, called a "calibration curve" m/z=f(x). Then a spectrum of the ions of an analyte substance can be measured and the masses m/z of the ions at a certain location x on the scale can be calculated using the calibration curve. For even more accurate mass measurements, one adds to the analyte substance one or more known mass reference substances and corrects the masses of the analyte substance using the mass differences, found for the mass reference substances between calculated and true masses (method with "internal mass reference").

The basis of all these calibration methods is always the exact determination of the precise scale parameter x for an individual peak on the spectrum scale axis. Any spectrum acquired by a mass spectrometer consists of a large series of individual digital values, either measurement values or transformed measurement values, where the indices of the series represent the spectrum scale. For exact mass determinations, one must derive the accurate position, frequency, or time value from a measured (spatial or temporal) profile of the measured ion current values across a peak. Usually, the ion current peak consists of four to ten measurement values above background noise. In the simplest case a centroid formation of the individual measured values is used. In more elaborate but more accurate methods a theoretically derived or experimentally determined function is fitted into the measured profile of a mass peak, from which the optimal positions, frequencies or time values of the peaks are derived.

In the following, we shall restrict the description for reasons of clarity to time-of-flight spectra only; this should, however, not mean that the invention will be restricted to this type of spectra. In modern time-of-flight mass spectrometers (TOF-MS), single spectra are obtained in 50 to 200 microseconds, using measuring rates up to 4 gigasamples per second and more. The acquisition of single spectra is repeated 5,000 to 10,000 times per second; the series of 200,000 to 800,000 measuring values are added in real time, value for value over a predetermined time period to yield a sum spectrum in which the signal-to-noise ratio is greatly improved and the dynamic measuring range is enlarged. The determination of the exact flight time of the ions of a peak is then performed using the series of summed measuring values of this sum spectrum. The flight time determination of a peak constitutes the main source of inaccuracies of the mass determination.

For more complex substances, as for biopolymers like peptides, measured with sufficient mass resolutions R, the spectrum of the molecular ions always shows several peaks with ions of the same elemental but different isotopic composition, the peaks being one atomic mass unit apart from each other. These peaks are called here an "isotope group". FIGS. 1 to 3, which show ion current peaks versus a scale factor x, present three examples for peptides with masses of 1,000, 2,000 and 3,000 dalton, respectively. The lightest ions form the "mono-isotopic peak" of the group, composed only of $^1H$, $^{12}C$, $^{14}N$, $^{16}O$, $^{31}P$ and $^{32}S$. There are methods to calculate the exact form of the isotope group of peaks from the elemental composition and the known isotope abundances of the elements, but these calculations are rather complicated and slow.

In document U.S. Pat. No. 6,188,064 B1 (GB 2 333 893 B; DE 198 03 309 01; C. Koester, 1998), a highly precise method is described for the determination of the flight time of the mono-isotopic peak, using a process of fitting a whole family of superimposed bell-shaped curves of known mass distances and averaged peak height relations into the measured signal pattern of the complete isotope peak group, instead of fitting just one single bell-shaped curve into a measured signal profile of a single ion peak. This method has become widely known by the name "SNAP". The method is directed to an exact determination of the masses of ions of unknown substances for their identification. While the substances themselves are unknown, the class of substances, e.g., proteins, is generally known. Therefore, the peak height distribution of the isotope group is calculated as an average for the class of substances, using an average of the elemental composition of that class and the known isotope abundances of the elements. As can be seen from FIGS. 1 to 3, the average peak height distribution is strongly dependent on the mass of the ions. Therefore, a series of averaged peak height distributions is calculated once for ions of different masses of this class of substances, stored in a table, and used over and over, calculating the averaged peak height distribution at a given mass by interpolation from the stored distributions in the table. This procedure saves time, because the calculation of peak height distributions from averaged elemental composition and isotope abundances is rather complicated and cannot be performed for each isotope group in a complicated spectrum in an acceptable time span.

Coming back to the determination of peptide concentrations, to improve the precision of the analysis procedure, the readily available SNAP procedure was applied to the isotope groups of target and reference peptide. Regrettably, however, no improvement of the precision could be observed.

A highly precise procedure is still sought for the determination of the ratio of the target peptide ion current to the reference peptide ion current, represented by the detectable peaks in the measured spectrum and used for the quantitative analysis of peptides in fluids. Because the analytical procedure should also be used for diagnostic purposes, it is a most essential requirement to enable the procedure to recognize, by built-in quality indicators, any technical faults and disturbances in each individual analysis.

SUMMARY

In accordance with the principles of the invention, the concentration ratio of a target analyte peptide to an isotopically labeled reference peptide is determined from the spectrum of the extracted peptides by a curve fitting method similar to the "SNAP" method, however, in a severely modified form, because (1) the rather small peptides show strong individual deviations of the isotopic distribution from the average for larger proteins, and (2) the isotopes used for labeling are never isotopically pure and produce a rather complex isotope peak pattern for the reference substance. Thus, in one embodiment, individual isotope distribution patterns are calculated for each target and reference peptide, the pattern for the reference peptide taking into account the impurity of the isotopes used for labeling. The individual isotope distribution patterns can be calculated from the elemental composition of the peptides and the isotope abundance distributions of the elements, taking into account the purity of the isotopes used for labeling, or from mass spectra acquired for the peptides.

A diagnostic method must fulfill strong quality standards. The precise curve fitting procedure according to the invention has the big advantage of automatically delivering several quality indicators. First, the fit delivers an exactly (accurately) measured mass of the target peptide, from which a "recognition quality indicator" may be derived, comparing the measured mass with the true mass. Second, from the quality of the fit, an individual "analysis quality indicator" can be derived for each individual analysis, indicating freedom of any superposition with ion peaks of other substances. Third, the widths of the best fitting curves automatically deliver the resolution of the mass spectrometer, which represents an "instrument quality indicator" for a correct adjustment and operation of the instrument. For all three quality indicators, tolerance values may be set, ensuring a correct analysis.

A further means to check the correctness of the analysis is the common measurement of key fragment ions of both the target peptide and the reference peptide ("reporter fragment ions") wherein their ion current relation must be the same as for the peaks of the target and the reference peptide. The invention, therefore, uses a method to acquire fragment ion spectra with a small range of masses, covering fragment ions of the target peptide and the reference peptide in a single fragment ion spectrum, which can be performed in simple MALDI-TOF-MS with reflectors. If the fragment ion spectra yield the same ratio of the fragment ion currents compared to the ratio of the unfragmented ion currents, a correct measurement of the unfragmented ions is strongly confirmed.

The ion current of a complete isotope peak group is determined by simultaneously fitting a whole family of superimposed bell-shaped curves to the measured peak pattern of the complete isotope group. The bell-shaped curves may be Gaussian distribution curves, which produce good fits for most mass spectrometers, or may be other mathematical curves derived on the basis of measured peak profiles. The bell-shaped curves may also be derived from mass spectra acquired for the peptides. The height relations of the superimposed bell-shaped curves, and their distances from each other, must be kept fixed during the fit and must correspond to the height distribution and distances of the isotope pattern, which has been exactly calculated individually for the target and the reference peptide.

The fitting procedure is easiest performed by finding the minimum of the sum of squared differences between measured ion current values and the values calculated from the family of bell-shaped curves forming the isotope peak pattern. For the fitting, a shift value along the spectrum scale, a curve width factor, and a curve height factor are varied as fitting parameters. There are several types of multi-parameter fitting procedures with different kinds of merits known in statistical mathematics.

The integrated ion currents of the isotope peak groups, representing the concentrations of the two peptides, are then determined by integration over the bell-shaped curves. A calibration of the analysis procedure with several different concentration ratios of target to reference peptide takes into account any non-linearity between the ion current ratio and the concentration ratio.

In another embodiment of the invention, the isotope groups of target and reference peptide are jointly fitted, the relative heights of both families of bell-shaped curves being a further fitting parameter, and the exactly known distance of both families being kept fixed. This procedure increases the dynamic measuring range because even peak groups of small height may be safely recognized and fitted. The quality of this joint fit results in a still better quality indicator for the individual analysis. The additional fitting parameter directly represents the ratio of the integrated ion currents of target and reference peptide, representing the concentration ratio.

The analysis may be performed with any mass spectrometer offering sufficient mass resolution, and any ionization method offering sufficient ionization reproducibility. A preferred combination is a MALDI time-of-flight mass spectrometer (MALDI-TOF-MS) with reflector, offering mass resolutions between R=6,000 and R=10,000. MALDI-TOF-MS with these specifications are commercially available as bench-top instruments.

Thus, the invention comprises a method to determine the concentration ratio of a target peptide to an added reference peptide in a fluid by acquiring a spectrum of the extracted peptides in a mass spectrometer and by fitting families of superimposed bell-shaped curves, each with fixed height distributions and fixed distances from each other, to the peaks of the isotope peak groups of the target and the reference peptide. The reference peptide is chemically identical with the target peptide, but isotopically labeled. The fixed curve height distributions and curve distances in the families of the bell-shaped curves for the target peptide and the reference peptide are individually calculated from the known elemental composition of the peptides and the isotope abundance distributions of the elements, taking into account the purity of the isotopes used for labeling.

The fitting process may be performed by variations of a shift parameter along the spectrum to match the peak maxima, a height factor for all bell-shaped curves of a family, and a width factor for all bell-shaped curves. The two families of bell-shaped curves, each with fixed curve height distributions, but with exactly known distance of the two families, may be fitted jointly to the target peptide isotope peak group and the reference peptide isotope peak group, varying an additional parameter for the ratio of the curve heights of the two curve families. An additional fitting parameter may characterize the purity of these isotopes and may be varied during the fitting process, if the abundance distribution of the isotopes used for the labeling is not exactly known. Additionally, a background level parameter may be varied during the fitting process.

In still another embodiment, the fitting process searches for the minimum of the sum of the squared deviations between curve values and measured ion current values. The bell-shaped curves may be Gaussian distribution curves or may be curves describing the measured peak profiles.

From the minimum of the sum of squared deviations in relation to the total areas of the bell-shaped curves, an individual "analysis quality indicator" may be derived. An individual "recognition quality indicator" may be derived from a comparison of the measured and the true mass of the target peptide, the measured mass derived from the optimum shift parameter along the mass spectrum. An individual "instrument quality indicator" is derived from the optimum widths of the curves used for the fitting process.

The concentration ratio of target and reference substance is, for example, represented by the ratio of the integrated ion currents of target and reference peptide; the latter can be determined by the ratio of the areas of the best fitting curve families for target and reference peptides. A computer program may evaluate the spectrum and automatically calculate the ratio of the integrated ion currents of the isotope groups of the target and the reference peptide. The method may be calibrated using different ratios of target peptide and reference peptide; and the concentration of more than one target peptide may be analyzed in a single sample preparation and spectrum measurement procedure.

Additionally, a spectrum of selected key fragment ions of both the target and the reference peptide may be acquired and evaluated. The key fragment ion spectrum may be used to confirm the evaluation of the unfragmented ions.

The peak height distributions for the curve families of a given target peptide and its reference peptide may be calculated once and stored in a table for further use. A computer program for the evaluation of peptide spectra may have access to the table of computed height distributions for different target peptides and their reference peptides.

The complete method to determine the concentration ratio between a target substance and a reference substance in a sample, the reference substance being chemically identical with the target and isotopically labeled, may be described by the following steps:

a) extracting the target substance and the reference substance from the sample,
b) acquiring a mass spectrum with mass signals of the target substance and the reference substance,
c) fitting a first group of peaks to the mass signals of the target substance and a second peak group to the mass signals of the reference substance, wherein the peaks of each group have a fixed relative height and distance and wherein the relative height of the peaks are individually determined, and
d) determining the concentration ratio from parameters of the fitting.

The relative height of the peaks of the first group should be individually determined, either by calculation from the elemental composition and the isotope abundance distributions of the elements, or from a measured mass spectrum of the target substance and the reference substance. Both groups of peaks can be mathematical functions, or can be obtained from measured mass spectra of the target substance and the reference substance, respectively.

The sample may be a body fluid, a homogenized tissue sample or a tissue prepared for mass spectrometric MALDI imaging, and the target substance may be a peptide, a drug or a metabolite of a drug.

BRIEF DESCRIPTION OF THE DRAWINGS

FIGS. 1, 2 and 3 present conventional examples of calculated height distributions of isotope peak groups for three distinct target peptides with molecular masses of 1,000, 2,000 and 3,000 dalton respectively. The figures also show the expected increase in peak width for heavier ions. In FIG. 3, the monoisotopic (first) peak is no longer the largest. There are more peaks with higher masses for each of the peptides, but their heights are below the threshold for detection. Negligence of the undetectable peaks does not deteriorate the accuracy of the method.

DETAILED DESCRIPTION

Figure 4:
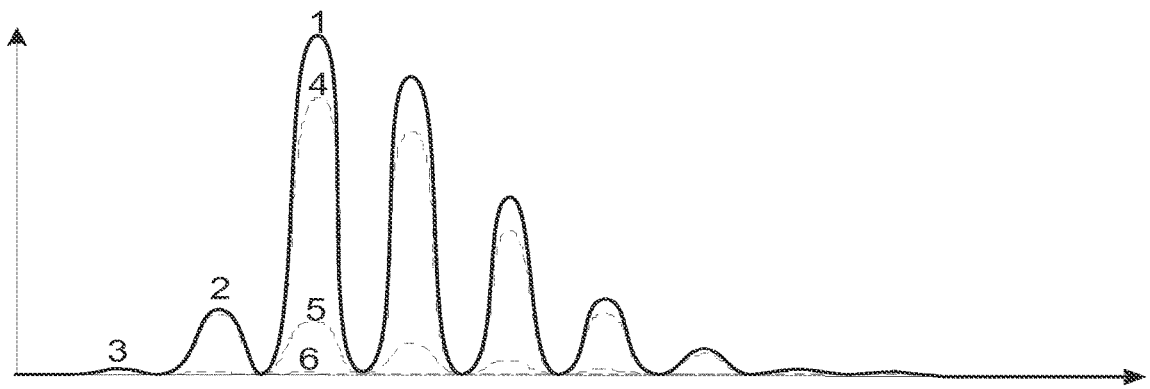
FIG. 4 shows the superposition of three identical isotope peak groups of an isotopically labeled reference peptide with lacking purity of the isotopes used for labeling, forming a "pre-peak" (2) and a "pre-pre-peak" (3) on the low mass side of the main peak (1). The main peak (1) is no longer a truly monoisotopic peak, because it is composed of the superimposed peaks (4), (5) and (6), originating from differently shifted isotope patterns with different numbers of labeling isotopes. The purity for the ten isotope atoms used for labeling is assumed to be 98 percent, resulting in a pre-peak (2) of roughly 20 percent in height relative to the main peak (1), and a pre-pre-peak (3) of about 0.4 percent.

The invention applies mass spectrometry to determine the concentration ratio of a target peptide in a fluid to an added reference peptide, from a spectrum of the jointly extracted peptides as precisely as possible, and uses the ratio of the integrated ion currents of all detectable peaks of the complete isotope peak groups of the analyte peptide and the reference peptide in a spectrum instead of only comparing single ion peaks. The invention proposes to determine the ratio of the integrated ion currents by fitting families of bell-shaped curves to the peaks in the spectrum, with curve height distributions identical to the exactly calculated isotope distributions of the individual target and the individual reference peptide, the isotope distribution for the reference peptide taking into account the purity of the isotopes used for labeling. Examples for the isotope pattern of distinct peptides with molecular masses of 1,000, 2,000 and 3,000 dalton are displayed in FIGS. 1 to 3. As reference peptide, an isotopically labeled peptide, chemically identical with the target peptide, must be used for the invention.

A diagnostic method must fulfill strong quality standards. It is the biggest advantage of the precise curve fitting procedure according to the invention to deliver automatically several quality indicators. First, the fit delivers an exact value for the measured mass of the target peptide, from which a "recognition quality indicator" may be derived, comparing the measured mass with the true mass. Samples with a mixture of tuning substances may be used on each MALDI sample plate to check the validity of the mass calibration curve. Second and most important, an individual "analysis quality indicator" can be derived for each individual analysis from the quality of the fit, i.e., from the minimum sum of squared deviations in comparison to the integrated area of the fitting curves, indicating freedom of any superposition with ion peaks of other substances. Third, the width of the curves best fitting the measured ion current values automatically delivers a value for the resolution of the mass spectrometer, which represents an "instrument quality indicator" for a correct adjustment and operation of the instrument. Any false adjustment or any false operation of the mass spectrometer immediately deteriorates the mass resolution. Tolerance values for all three quality indicators ensure a correct analysis.

The invention proposes an additional means to check the correctness of the analysis by a measurement of key fragment ions of both the target peptide and the reference peptide ("reporter fragment ions") in a single fragment ion spectrum. The reporter fragment peaks must show the same ion current relation between peak groups for the target and the reference peptide. The acquisition of fragment ion spectra in a small range of masses, covering target and reference reporter fragment ions in a single fragment ion spectrum, can be performed in simple MALDI-TOF-MS with reflectors. The method is described in document US 2008/0296488 A1 (GB 2 456 022 A; DE 10 2007 024 857 A1; A. Holle, 2007). If the fragment ion spectra yield the same ratio of the reporter ion currents, a correct measurement of the unfragmented ions is strongly confirmed.

An example of a simple analytical procedure is described here in some detail concerning the determination of a peptide concentration in a body fluid; for example, blood plasma or liquor. More sophisticated analysis procedures will be given below. The simple procedure starts with an exactly known amount of body fluid, and adds a solution with an exactly known amount of reference substance. The reference peptide should be chemically identical to the target peptide, but isotopically marked. As an example, a reference peptide may be produced by exchanging, within a peptide identical to the target peptide, an arginine with normal isotope distribution by an arginine with six $^{13}$C and four $^{15}$N atoms. This arginine is heavier than the normal arginine by 10 atomic mass units.

After thorough mixing, both target and reference peptides are then extracted from the body fluid by immobilized antibodies. The antibodies may be immobilized at the wall of the container, or, in one embodiment, on the surfaces of magnetic beads which are added to the body fluid. Immobilization methods are well-known; magnetic beads readily prepared for the immobilization of antibodies are commercially available. It is not required that the antibodies are completely free of reacting with other substances, some degree of cross-reaction can be tolerated because the mass spectrum will easily show and separate the cross-reaction products. It is rather expensive to produce antibodies for small peptides showing no cross-reactions (if at all possible), so much less expensive antibodies can be used here without severe drawbacks, provided they have a dissociation constant low enough that the peptides do not dissociate from the antibody during the washing procedure. The extraction process extracts both peptides in equal proportions, even if the extraction is incomplete. The extracted peptides, therefore, have exactly the ratio of the amount of target peptides in the body fluid to the amount of added reference peptides.

The peptides are then dissolved again by removal from the antibodies by known methods, and concentrated by solvent evaporation if necessary. About one microliter of this extract is then prepared on a sample spot covered with a thin layer of HCCA on a commercial target plate with 384 pre-prepared sample spots. The micro-crystalline layer immediately adsorbs the peptides from the extract. After about two minutes, the residual liquid can be taken away and a wash solution can be added and removed, removing thereby most impurities which may disturb the ionization process. The dried layer of HCCA micro-crystals may then be partly re-crystallized by a solvent, providing a very homogeneous embedding of the peptides within the thin crystal layer.

The readily prepared MALDI target plate is introduced into the ion source of a suitable mass spectrometer. Flashes of UV laser light generate small plasma clouds in which the peptides are ionized. In some commercially available mass spectrometers, the UV laser beam is divided and focused into about 20 small laser spots, each less than 10 micrometers in diameter (U.S. Pat. No. 7,235,781 B2; GB 2 421 352 B; A. Haase et al., 2004). This allows for a relatively high energy density in each of the spots, achieving a high ionization yield of the analytes and low sample consumption. With correct energy density, a single laser flash produces just enough ions for the acquisition of a single time-of-flight spectrum without saturating the ion detector. With laser flash rates of 5 to 20 kilohertz, 5,000 to 20,000 time-of-flight spectra per second are obtained. The measurement values of the ion currents of the single spectra are added in real time to form a sum spectrum with high signal-to-noise ratio and high dynamic measurement range. Usually, several thousand single spectra are added in less than a second, while the laser spots move across the sample area on the MALDI sample plate, averaging the signals from any inhomogeneities. The sum spectrum consists of a series of many thousands of measurement values, added up over all single spectra obtained.

The peptide peaks in the sum spectrum are then evaluated according to this invention by an optimization process, consisting of simultaneously fitting a whole family of superimposed bell-shaped curves to the peak pattern of a complete isotope group with exactly calculated height distributions and calculated distances of the curves from each other. Depending on the shape of the peak profiles, the bell-shaped curves may be Gaussian distribution curves, or other symmetric or asymmetric bell-shaped functions based on measured peak profiles. The distances between the bell-shaped curves are calculated from the known mass distances in the isotope group, using the inverse of the mass calibration function.

The invention is based on the experimental observation, that the statistically obtained distributions of peak heights for the class of proteins, successfully used in the SNAP procedure for precise mass determinations of unknown peptides and proteins, do not reflect the true distributions of individual peptides precisely enough for an application in quantitative analyses. Therefore, the heights of the bell-shaped curves relative to each other have to be calculated, for the target isotope group as well as for the reference isotope group, from the exactly known elemental composition of the target peptide and the reference peptide, and the known isotope distributions of the elements. For the reference peptide, the purity of the isotopes used for the labeling should be known; but this is not absolutely necessary because any unknown degree of impurity can be taken into account by an additional fitting parameter included in the optimization process.

Using the example of a labeled arginine given above, the isotope peak group of the reference peptide should have an almost identical pattern as the peak group of the target peptide, if the purity of the six $^{13}$C and four $^{15}$N isotopes used for the labeling of an arginine is 100 percent in both cases; the exact shape of the pattern can be calculated by the known isotopic composition of the reference peptide. In most cases, however, the isotopes used for the labeling are not pure; best isotope purities at affordable prices are in the range of 98 to 99.5 percent. If the purity of all ten $^{13}$C and $^{15}$N isotopes of arginine have only 98 percent purity, the rest being $^{12}$C and $^{14}$N, then a total of 20 percent of all reference ions have only a distance of 9 dalton from the corresponding target peptide ions instead of 10 dalton. This can be understood as a superposition of two exactly identical isotope peak patterns for the reference isotope peak group, calculated with pure isotopes, the two isotope peak patterns having a distance of one atomic mass unit. This situation can be recognized by the existence of a "pre-peak" the height of which is about 20 percent of the first peak of the peak group.

If the purities of $^{13}C$ and $^{14}N$ are exactly known, again the complex pattern can be calculated, and this pattern can be used for the fit. If the purities are not known, a superposition of the two patterns can be calculated, one pattern lacking one labeling isotope, the ratio of superposition calculated from the height of the pre-peak in relation to the first main peak. If the purity is still lower, than a third pattern lacking two labeling isotopes has to be superimposed, the height estimated from a "pre-pre-peak". This situation is shown in FIG. 4.

The isotopic labeling is not restricted to replacements of $^{12}C$ or $^{14}N$ by $^{13}C$ or $^{15}N$; in principle, $^2H$ (deuterium), $^{18}C$ or even $^{34}S$ may also be used for labeling. A minimum of three replacements with at least 3 dalton mass difference should be applied; the isotopic labeling may go up to replacing all $^1H$, $^{12}C$, $^{14}N$, $^{16}O$, or $^{32}S$, or any combination thereof. If a "proteotypic peptide" as the target peptide is produced by cleavage of a target protein (see below), the reference protein should be labeled correspondingly; the reference peptide will then be obtained by the cleavage of the reference protein. Sometimes reference peptides are obtained by a cleavage of a larger isotopically labeled protein, for instance, by a protein which was labeled during synthesis with 98% $^{15}N$. This may result in reference peptides with high number of atom replacements, shifting the mass away from the mass of the target peptide.

If the purities of the labeling isotopes are not known, the impurity can also be considered by the fitting procedure, introducing the ratio of the superposition of the patterns, as shown in FIG. 4, as a further fitting parameter. From the ratio of the pre-peak to the main peak, a start value for the optimization procedure may be obtained.

In one embodiment of the analysis procedure, the fitting procedure may be performed twice: once for the target peptide isotope group, and once for the reference peptide isotope group. Then both fitting procedures are optimization processes with basically three parameters each: the flight times of the ions to move the pattern along the flight time axis, a width factor of the bell-shaped curves (the peak resolution), and a height factor of the exactly calculated pattern of bell-shaped curves. If the purity of the labeling isotopes is not exactly known, a fourth fitting parameter for the purity can be used.

This embodiment for the fitting procedure separately applied to the target and to the reference peptide isotope groups, however, is not the best approach. A more preferred embodiment of the optimization procedure fits both isotope groups of the target peptide and the reference peptide jointly in one single optimization procedure, introducing the integrated ion current ratio of target and reference peptide as a further fitting parameter. The mass difference between the two isotope groups, and consequently the flight time difference, is exactly known and is kept fixed by the joint optimization. The resulting integrated ion current ratio immediately represents the concentration ratio of target and reference peptide. This procedure of jointly fitting target and reference isotope groups increases the dynamic measuring range because peak groups of small height, scarcely visible in the spectrum, may be safely recognized by the clearly visible other isotope group and fitted. In addition, the quality of this joint fit results in a better analysis quality indicator for the individual analysis.

Before the fitting procedure is applied, an averaged background of the spectrum may be subtracted. Background subtraction procedures are well-known to the specialist in the field. However, background subtraction does not have to be performed, if the background level is introduced as a further optimization parameter. In this case, the families of superimposed curves should be prolonged in both directions by straight lines, which will be fitted to the background. This procedure, in fact, is most preferred because any manipulation of the originally measured ion current values of the spectrum is avoided. Any manipulation like background subtraction or smoothing, may falsify the results in a non-tractable and non-reproducible manner.

The fitting procedure is usually performed by finding the minimum of the sum of squared differences between measured values and the correspondent values of the fitting pattern, varying the fitting parameters. There are several mathematical algorithms known for fast multidimensional fitting procedures, each showing different merits like, e.g., speed of calculation or ability to find the correct minimum in the multidimensional space, if there are several minima. Any one of these methods may be used for the invention. As fitting procedures for the bell-shaped curves it is not only possible to use the search for the smallest sum of squared deviations, but also to use correlation calculations (maximizing correlation), or fitting procedures using Fourier transformations. The method using the smallest sum of the squared deviations, however, has proven to be the best and easiest so far.

The simple example of an analysis procedure described so far began with a single volume of body fluid, and adding a single amount of the isotopically labeled reference peptide. A more sophisticated procedure increases both the dynamic range and the precision of the analysis. This more sophisticated procedure starts with a sample preparation which uses a series of dilutions of the body fluid with different concentrations. For example, a dilution series of the body fluid with eight dilution steps of 1:2:4:8:16:32:64:128 may be used. To each of the eight vials with diluted body fluid, an identical amount of reference substance is added, if possible, with a concentration of the reference peptide corresponding to the expected target peptide concentration in the vials with 1:8 or 1:16 dilution. This takes 8 of the 384 spots on the MALDI target plate, allowing the analysis of peptides in 48 different samples of body fluids in parallel. If each of the 384 samples on the MALDI target plate is measured for a full second, the complete measurement takes less than ten minutes. Usually, all calculations for the evaluation of the spectra are performed in real time. At the end of the measurements, all analytical results are available. This process with dilution series yields very precise determinations of the peptide concentrations, even if a strong deviation by factors of ten from the expected peptide concentration is observed in the body fluid, because for each target peptide concentration, there is a measurement with a reference peptide with about the same concentration. These measurements with about the same concentration for target and reference peptide show the highest precision. Of course, the dilution series may be correspondingly adapted if the concentration range, in which the target peptide may be expected, is larger or smaller.

It should be noted, that the evaluation in real time makes it possible to repeat measurements for a distinct sample, if the spectrum does not have the required quality. For example, a spectrum acquisition may be repeated with ten seconds acquisition time instead of only one second, if the signal-to-noise ratio for the first measurement proved to be not high enough.

Figure 5:
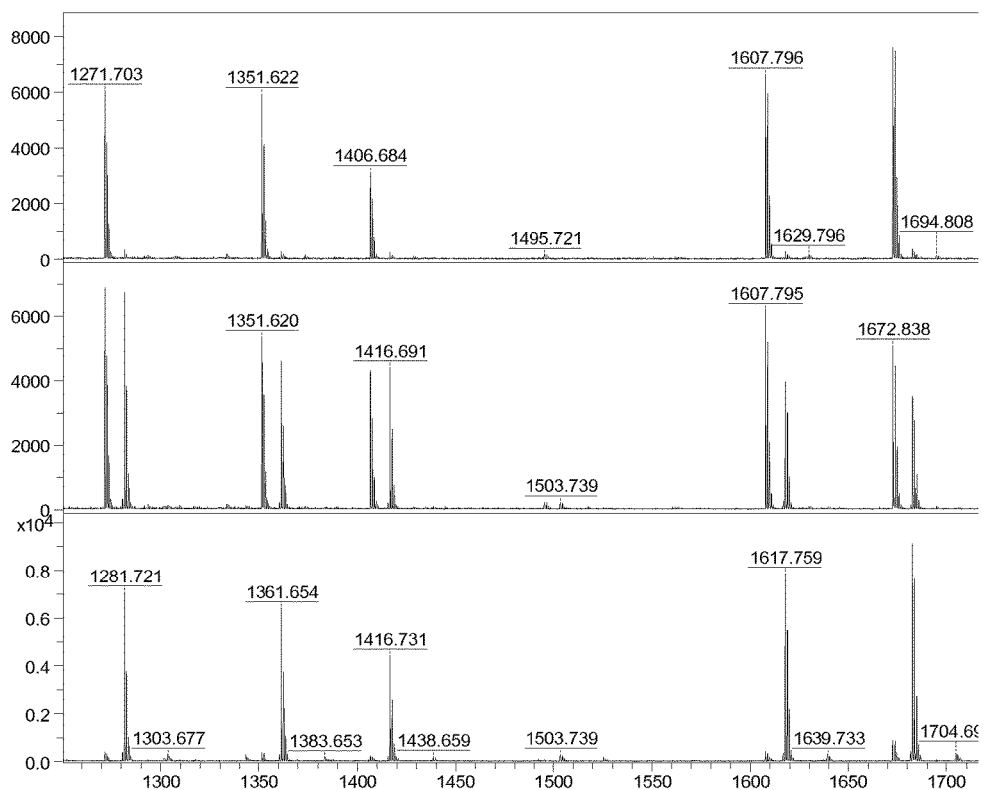
FIG. 5 shows three mass spectra with five analyte peptides and their reference peptides each, for concentration ratios of 10:1, 1:1, and 1:10. Pre-peaks can be seen for each of the reference peptides. The spectra are selected from a multiplex analysis calibration.
Figure 6:
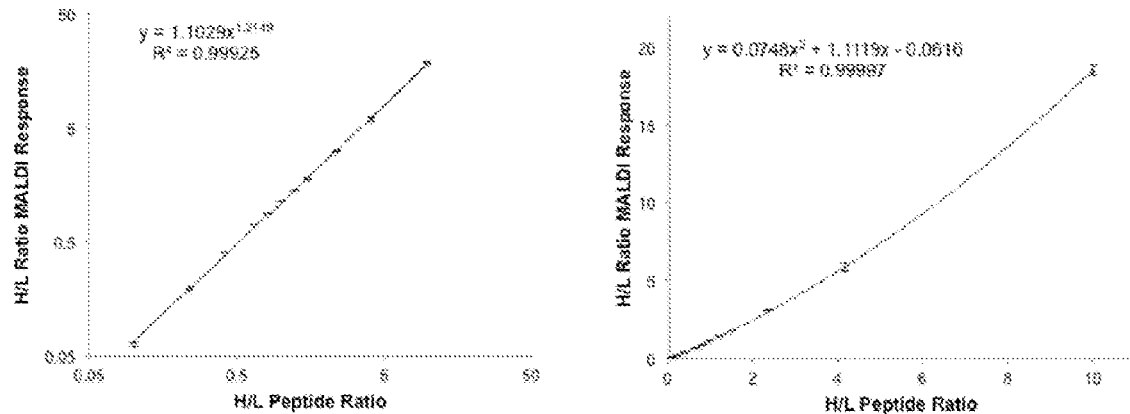
In FIG. 6, the calibration curve for one of the peptides of FIG. 5 is presented, in logarithmic and linear form. The resulting accuracy of the determination of the concentration is around 2 percent (CV=0.02) in the range between 3:1 and 1:3, and better than 5 percent in the full range. The curve demonstrates excellent quantification by the analysis procedure. The calibration curves for the other four peptides are similar in quality.

Up to now, we have directed our view to obtain highly precise analysis procedures. To achieve a highly accurate analysis, any precise method can be calibrated. For a calibration, the ratio of the integrated ion currents $i_t/i_r$ for target and reference peptides can be measured precisely for various exactly known concentration ratios q for target and reference peptides, and a multipoint calibration curve $q=f(i_t/i_r)$ can be determined. The concentration ratios q may be changed, for example, from q=1:10 to q=10:1. FIG. 5 exhibits three mass spectra with five analyte peptides and their reference peptides each, for concentration ratios of 10:1, 1:1, and 1:10. The three spectra are selected from a full series of calibration spectra. In FIG. 6, the resulting calibration curve for one of these peptides is presented. As a result, the accuracy of the determination of the concentration is around CV=0.02 (2 percent) in the range between 3:1 and 1:3, and better than 5 percent in the full range. CV is the coefficient of variation, as defined in the field of statistics. If the analysis procedure using dilution series is applied for such determinations, as described above, the overall accuracy then is better than 2 percent in a wide concentration range over two orders of magnitude. This is an unusually good accuracy for any quantitative determination of peptides in body fluids, made possible by the invention.

Figure 7:
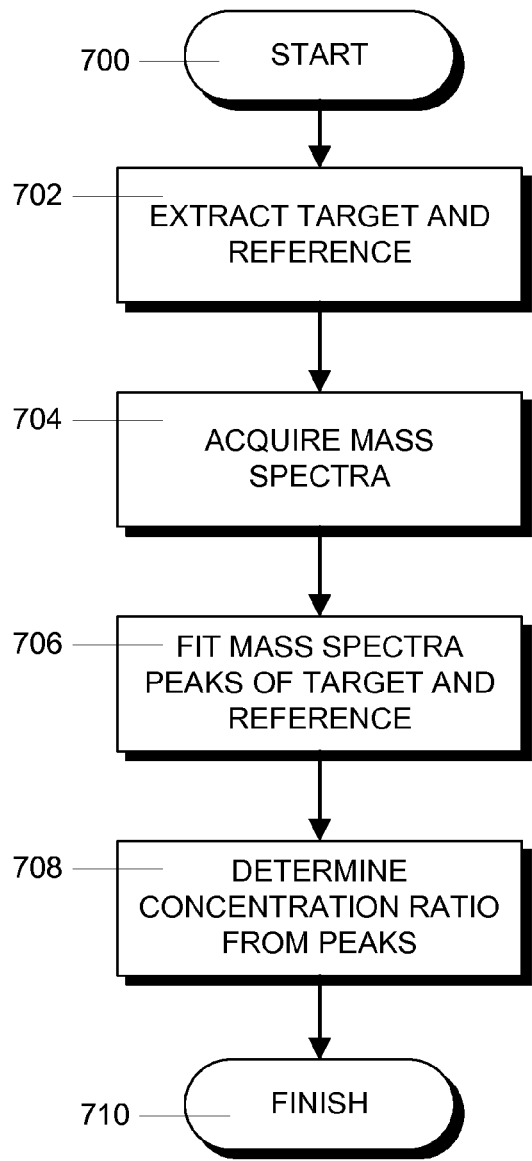
FIG. 7 is an illustrative flowchart showing the steps in a method for quantitative peptide analysis in accordance with the principles of the invention.

FIG. 7 shows the steps in an illustrative process in accordance with the principles of the invention. The process starts in step 700 and proceeds to step 702 where the target substance and the reference substance are extracted from the sample. Next, in step 704, a mass spectrum with mass signals of the target substance and the reference substance is acquired. Then, in step 706, a first group of peaks is fitted to the mass signals of the target substance and a second peak group is fitted to the mass signals of the reference substance, wherein the peaks of each peak group have a fixed relative height and distance and wherein the relative height of the peaks are individually determined. Then, in step 708, the concentration ratio of the target substance to the reference substance is determined from parameters of the fitting.

The analysis procedures outlined so far were directed to the concentration analysis of a single peptide in the body fluid. The concept, however, may be easily widened to include multiplex analyses for several different target peptides in the same sample, with evaluation of all target peptide concentrations from the same spectra. In a preferred embodiment of a multiplex analysis, this method is calibrated commonly for all different target peptides. An example for a multiplex analysis is shown in FIG. 5, where five different target peptides are commonly calibrated.

As already mentioned above, it is the biggest advantage of this invention with precise curve fitting to deliver automatically, from the quality of the fit, an "analysis quality indicator" for each individual analysis. This quality indicator indicates the absence of any superpositions of the target and reference peptide isotope groups with any ion peaks of other substances. In general, such superpositions with peaks of other substances are rare because the specific extraction, e.g. with antibodies, widely purifies the extracted peptides from pollutions, and residual pollutions rarely have the same masses as the target peptides. The analysis quality indicator for the fit may be derived from the minimum of the sum of squared differences, for instance, the indicator may be formed by the ratio between the square root of the minimum of the sum of squared differences and the area under the bell-shaped curves. If the bell-shaped curves nicely reflect the shape of the peaks, this ratio should be far less than 1%, in good fits much less than 0.1%. This analysis quality indicator clearly reveals any superposition with peaks of other substances, which immediately increases the minimum sum of squared differences, particularly in the most preferred case of a joint fitting of theoretical curves to target and reference peptide isotope groups.

It should be noted, that a deconvolution may be tried, if the analysis quality indicator indicates any superposition with peaks of another substance. In most cases, not all peaks suffer similar superpositions; the isotope pattern of the target peptide (or its reference) and the isotope pattern of the pollution usually will be shifted against each other, allowing for such a deconvolution. The precision of such an analysis by deconvolution may suffer greatly, but at least there will be a result for this analysis. The deconvolution may be performed automatically by a computer program; deconvolution methods are known to the specialist in the field.

In addition, two more quality indicators are automatically delivered by the fitting procedure. The width parameter of the best fitting curves automatically reflects the resolution of the mass spectrometer, which represents an "instrument quality indicator". Any wrong adjustment, or any wrong operation, will immediately reduce the mass resolution of the instrument and becomes visible by this instrument quality indicator. And the precise value for the mass of the target peptide, delivered by the scale shift fitting parameter, represents a "recognition quality indicator". If the validity of the calibration curve is checked repeatedly, for instance, by a tuning mixture of substances in an extra sample spot on each MALDI target plate, then this recognition quality indicator shows a correct identification of the target peptide. In usual MALDI-TOF-MS, the accuracy for mass determinations is in the range of 10 to 30 parts per million (ppm). If the evaluation of the spectra is performed automatically by computer programs, thresholds or tolerance values for all three quality indicators ensure the validity of the result of each individual analysis.

The description of the invention was based on MALDI time-of-flight mass spectrometry; however, the analysis may be performed by any mass spectrometer offering sufficient mass resolution and mass range, and any ionization method offering sufficient ionization reproducibility. An inexpensive mass spectrometer, for instance, is an RF ion trap mass spectrometer with MALDI ion source, but there are numerous other combinations of ion sources and mass spectrometers. The most preferred combination is a rather small and inexpensive MALDI time-of-flight mass spectrometer (MALDI-TOF-MS) with reflector, offering mass resolutions between $R=m/\Delta m=6,000$ and R=10,000, $\Delta m$ being the width of the peak at half height. MALDI-TOF-MS with these specifications are commercially available as bench-top instruments. There are even bench-top MALDI-TOF-MS approved for diagnostic purposes in medical institutions.

As stated above, any diagnostic method used in medicine must fulfill strong quality standards. Not only the instrument has to be approved by official organizations, the analytical procedure has to be approved, too. The analysis procedure described here should fulfill any of these requirements because the procedure has built-in supervisory means for the correct recognition of the target peptide, for the quality of each individual analysis, and for the function of the mass spectrometer. A safe recognition of the analyte and reference peaks is given by an accurate mass determination of the target peptide and particularly by a correct mass distance between the peak groups of analyte peptide and reference peptide. The isotope peak groups of analyte peptides and reference peak groups are expected to be, in general, free of superpositions with ion peaks of other substances, because the extraction step with antibodies or other affinity reagents widely purifies the target peptides. Cross-reactions of the antibodies are easily recognized by gross changes in the spectrum or even by subtle changes of the expected peptide isotopic groups. The quality indicator of the fitting procedure may be used as an additional measure to ensure a correct quantification, a carefully selected threshold for this indicator should accept only such analyses which show a high quality.

The safety for a correct quantification can even be increased by a joint measurement of key fragment ions ("reporter ions") of both the target peptide and the reference peptide. A simple method to acquire fragment ion spectra in a small range of masses, covering target peptide fragment ions and reference peptide fragment ions, can be performed in MALDI-TOF-MS with reflectors. As already mentioned above, the method is described in document US 2008/0296488 A1 (GB 2 456 022 A; DE 10 2007 024 857 A1; A. Holle, 2007). The energy density in the laser spots is slightly increased, and ions of both isotopic groups are jointly selected by a parent ion selector. A fraction of these ions is metastable and these ions decay on their way to the reflector. The reflector voltage is decreased to reflect the selected reporter ions only; the detector now measures only the mass spectra of these reporter ions similarly to the well known single reaction monitoring (SRM) mass spectra on triple quadrupole instruments. Both reporter ion isotope groups for target and reference peptide stand out very clearly from a rather clean background, and the comparison of the integrated ion currents of both groups can be performed according to the invention.

The reporter ion spectra must display the same ratio of the integrated ion currents as the unfragmented ions to be confirmative of the initial MS measurements. The probability that a non-recognized superposition by another substance delivers exactly the same fragment ions is nearly infinitely small. In particular, non-equal widths of the peaks in the target peptide group and the reference peptide group indicate superpositions and this superposition can be confirmed by the SRM-like analysis.

The analytical procedure described here can be applied best to target peptides with about 8 to 25 amino acids, i.e., in the mass range from 1,000 to 3,000 dalton. If the peptides or proteins are larger, say up to 100 amino acids, an enzymatic or chemical cleavage should be applied. The well-known tryptic digestion forms digest peptides in the optimum mass range, but there are a variety of other enzymes like, e.g., lys C or chemotrypsin. Even a chemical treatment may be applied to cleave larger peptides or proteins, as, for instance, cyanogen bromide. The reference peptide or protein should be digested together with the target peptide or protein, and the antibody should extract a key digestion peptide called "proteotypic peptide".

For a fast performance of the mathematical fitting procedures, it is essential to begin with start values for the fitting parameters which are as near to the final values as possible. All start values can be automatically derived from the spectrum itself or from the calibration of the mass spectrometer. The start value for the flight time shift parameter of the monoisotopic peak can be calculated from the known mass by applying the inverse of the calibration function. The start values for the width and the height factors can be derived from the measured peak width and height of the monoisotopic peak. The start value for the isotopic impurity of the labeling isotopes can be estimated by the size of the pre-peak of the reference peptide isotope group, relative to the monoisotopic peak. The start value for the background noise can also be taken from the spectrum. The start value for the ratio of the integrated ion currents of target peptide and reference peptide can be determined by the peak heights of the monoisotopic peaks, the monoisotopic peak height of the reference peptide being corrected by the height of the pre-peak.

If the measured peaks are symmetric, a Gaussian distribution function can very simply be used as the bell-shaped curve, for instance. Another symmetric bell-shaped curve is the square of the Gaussian distribution. Fitting can be restricted to profile values above an averaged background (e.g. by background subtraction), or can include an optimization of a background level parameter. For asymmetric peaks, different profile functions are known to the specialist in the field.

The two groups of target peptide and reference peptide usually cover a mass range of about twenty daltons. Within this mass range, the widths of the single peaks can be assumed to be sufficiently constant. It is known, however, that the width w in most mass spectrometers weakly changes with flight time t approximately by a linear relation $w(t)=a+b \times t$, a and b being constants which can be experimentally determined once for a given mass spectrometer. If highest quality of the analysis procedure is required, this relation can be used to calculate the fixed width relations for the fit.

The calculation of the individual isotope pattern for a given target or reference peptide is certainly somewhat complicated but, for example, it can be obtained in a well-known manner using Fourier transformation, if the element and isotope composition is known. These calculations may be performed once for a target peptide and its reference peptide, and the results may be saved in tables and used again and again in future for analyses of this target peptide. The evaluation of the spectra may be performed in a completely automatic way by a computer program, using tables with isotopic compositions for many target peptides.

As a simplification, the distance between the peaks can always assumed to be 1.003355 dalton (the exact distance between carbon isotopes). The family of curves to be fitted is therefore relatively simple and easy to calculate—as only the flight time, the width factor of the bell-shaped curves, and a height factor for the height distribution of the curves are varied until the sum of quadratic deviations is at a minimum. This method leads to good results, at least in the interesting mass range of 800 to 5,000 dalton.

If the ionization of the peptides is not performed by MALDI, but by electrospray (ESI) instead, isotope groups of molecule ions with selected, multiple charges may be the basis for the analysis. It may even be possible to jointly fit isotope groups with several charges, including the ion charge z (typically $1 \leq z \leq 6$) in the fitting process. In this case, the additional proton per charge has to be considered for the calculation of the charge-related masses m/z.

If the basic idea of this invention is understood, any expert in this field will be able to find and conduct the best method for determining accurate peptide concentrations under the circumstances of his laboratory. Well developed standard operation procedures (SOP) according to the basic idea of this invention can also be easily integrated into software analysis programs for mass spectra, as delivered by producers of relevant mass spectrometers. The software inside the computer controlling the mass spectrometer and performing the SOP may comprise all data for a number of approved analysis procedures; in this case the user ultimately only needs to state the target peptide to achieve a fully automatic evaluation of the spectra with respect to quantitative analyses with an automated quality assessment of the information provided by the analysis. On the other hand, the software may be open for the addition of approved analysis procedures by the user, offering calculation procedures for calculation of the isotope abundance profile of a target peptide of given elemental formula, and of the reference peptide with given purity values, numbers and types of isotopes used for labeling.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for determining the concentration ratio of a target peptide in a sample to a reference peptide present in a known amount in a known amount of the sample, the target peptide and reference peptide each having a known elemental composition, and the reference peptide being chemically identical with the target peptide, but having a different isotopic composition, the method comprising:
   (a) extracting the target peptide and the reference peptide from the sample;
   (b) acquiring mass spectra of the extracted target and reference peptides in a mass spectrometer, the mass spectra having ion peak distributions specific to the target and reference peptides, respectively;
   (c) fitting a first family of superimposed bell-shaped curves to the ion peak distribution of the target peptide and a second family of superimposed bell-shaped curves to the ion peak distribution of the reference peptide by varying parameters of the families to find fitted parameter values that minimize differences between the families and the respective ion peak distributions, wherein, in each family, each bell-shaped curve has a predetermined relative height and the curves have fixed distances from each other, the relative curve heights and inter curve distances in the families for the target peptide and the reference peptide being individually determined from one or both of (i) previously measured peak profiles of target and reference peptides and (ii) the elemental composition of the peptides and the respective isotope abundance distributions of elements composing the target and reference peptides, taking into account the purity of the isotopes used for labeling,
      wherein one of the parameters is a height parameter that changes the height of all bell-shaped curves of a family; and
   (d) determining the concentration ratio from the fitted parameter values found in step (c) for each of the first and second families.

2. The method of claim 1, wherein varying parameters of the families in step (c) comprises:
   (c1) varying a shift parameter to shift each curve family in a spectrum scale direction relative to the ion peak distributions of the target and the reference peptides in order to match peak maxima of ion current peaks and curve peaks; and
   (c2) varying a width parameter that changes the width of all bell-shaped curves.

3. The method of claim 2, wherein a measured mass of the target peptide which is derived from a fitted parameter value for the shift parameter of step (c1) is compared with the true mass of the target peptide for deriving an individual recognition quality indicator as a measure for the correct identification of the target peptide.

4. The method of claim 2, wherein a fitted parameter value for the width parameter of step (c2) is compared to a predefined value for deriving an individual instrument quality indicator as a measure for correct adjustment and operation of the mass spectrometer.

5. The method of claim 1, wherein varying parameters of the families in step (c) comprises shifting the first and second families of bell-shaped curves in a spectrum scale direction relative to the ion peak distributions of the target and the reference peptides, each family having fixed curve height distributions, and the two families being separated in the scale direction by a predetermined distance in order to fit jointly the two curve families.

6. The method of claim 1, wherein step (c) comprises varying an additional parameter representing the degree of impurity of isotope atoms used for labeling the reference peptides during the fitting process when the exact isotope abundance distribution is not known, and wherein start values for the fitted parameter values are as near to final values as possible.

7. The method of claim 1, wherein step (c) comprises varying an additional parameter for fitting the superimposed bell-shaped curves to the background level of the ion peak distributions of the target peptides and reference peptides, respectively, including prolonging the families of superimposed curves in both directions by straight lines, which are fitted to the background.

8. The method of claim 1, wherein step (c) comprises varying said parameters of the families in order to minimize a sum of squared deviations between bell-shaped curve values and ion peak distribution values.

9. The method of claim 8, further comprising deriving an individual analysis quality indicator from a minimum of the sum of squared deviations and areas under the bell-shaped curves.

10. The method of claim 1, wherein the bell-shaped curves are Gaussian distribution curves.

11. The method of claim 1, wherein the bell-shaped curves are determined exclusively from previously measured peak profiles of target and reference peptides.

12. The method of claim 1, further comprising calibrating the method by performing the method with a plurality of predetermined concentration ratios of target peptide and reference peptide.

13. The method of claim 1, wherein the concentrations of a plurality of target peptides relative to a plurality of reference peptides in a single sample are determined by performing steps (a)-(d) once.

14. The method of claim 1, further comprising fragmenting the target peptide and the reference peptide and performing steps (a)-(d) on target peptide and the reference peptide ions.

15. The method according to claim 1, wherein the concentration ratio is determined from a ratio of the integrated areas of best fitting curve families of step (c).

16. A method to determine the concentration ratio between a target biomolecule and a reference biomolecule in a sample, the reference biomolecule being added in a known amount to a known amount of the sample, the target biomolecule and reference biomolecule each having a known elemental composition, and the reference biomolecule being chemically identical with the target biomolecule and isotopically labeled, comprising:
   (a) extracting the target biomolecule and the reference biomolecule from the sample;
   (b) acquiring mass spectra of the target biomolecule and the reference biomolecule, the mass spectra having ion peak distributions specific to the target and reference biomolecules, respectively;

(c) fitting a first group of peak curves to the ion peak distribution of the target biomolecule by varying parameters of the first group of peak curves to find fitted parameter values that minimize differences between the first group of peak curves and the ion peak distribution of the target biomolecule, and fitting a second group of peak curves to the ion peak distribution of the reference biomolecule by varying parameters of the second group of peak curves to find fitted parameter values that minimize differences between the second group of peak curves and the ion peak distribution of the reference biomolecule, the peak curves of each group having fixed relative heights and distances from each other that are determined from one or both of (i) previously measured peak profiles of target and reference biomolecules and (ii) the elemental composition of the biomolecules and the respective isotope abundance distributions of elements composing the target and reference biomolecules, taking into account the purity of the isotopes used for labeling, wherein one of the parameters is a height parameter that changes the height of all peak curves of a group; and (d) determining the concentration ratio from the fitted parameter values found in step (c) for each of the first and second group of peak curves.

17. The method of claim 16, wherein step (c) comprises determining the relative heights of the peak curves in the first and second groups exclusively by a calculation from an elemental composition and isotope abundance distributions of elements of the target biomolecule and the reference biomolecule.

18. The method of claim 16, wherein (c) comprises determining the relative heights of the peak curves in the first and second groups exclusively from previously measured peak profiles of the target biomolecule and the reference biomolecule.

19. The method of claim 16, wherein the sample is one of a body fluid, a homogenized tissue sample and a tissue prepared for mass spectrometric MALDI imaging.

20. The method according to claim 16, wherein the target biomolecule is one of a peptide, a drug and a metabolite of a drug.

21. The method according to claim 16, wherein the concentration ratio is determined from a ratio of areas of best fitting first and second peak curves of step (c).

22. The method of claim 16, wherein varying parameters of the groups of peak curves in step (c) comprises:

(c1) varying a shift parameter to shift each peak curve group in a spectrum scale direction relative to the ion peak distributions of the target and the reference biomolecules in order to match peak maxima of ion current peaks and curve peaks; and (c2) varying a width parameter that changes the width of all peak curves.

23. The method of claim 16, wherein varying parameters of the groups of peak curves in step (c) comprises shifting the first and second groups of peak curves in a spectrum scale direction relative to the ion peak distributions of the target and the reference biomolecules, each peak curve group having fixed curve height distributions, and the two peak curve groups being separated in the scale direction by a predetermined distance in order to fit jointly the two peak curve groups.

* * * * *